United States Patent
Suzuki et al.

(10) Patent No.: US 9,185,394 B2
(45) Date of Patent: *Nov. 10, 2015

(54) 3D DATA ANALYSIS APPARATUS AND 3D DATA ANALYSIS METHOD

(75) Inventors: Shunsuke Suzuki, Kanagawa (JP); Atsuo Fujimaki, Tokyo (JP)

(73) Assignee: Sony Corporation, Tokyo (JP)

( * ) Notice: Subject to any disclaimer, the term of this patent is extended or adjusted under 35 U.S.C. 154(b) by 123 days.

This patent is subject to a terminal disclaimer.

(21) Appl. No.: 13/989,000

(22) PCT Filed: Nov. 25, 2011

(86) PCT No.: PCT/JP2011/077196
§ 371 (c)(1),
(2), (4) Date: May 22, 2013

(87) PCT Pub. No.: WO2012/073825
PCT Pub. Date: Jun. 7, 2012

(65) Prior Publication Data
US 2013/0251242 A1   Sep. 26, 2013

(30) Foreign Application Priority Data

Dec. 3, 2010 (JP) ................................ 2010-269945

(51) Int. Cl.
| | |
|---|---|
| *G06K 9/00* | (2006.01) |
| *H04N 13/04* | (2006.01) |
| *G06T 19/20* | (2011.01) |
| *G01N 15/14* | (2006.01) |

(52) U.S. Cl.
CPC ........... *H04N 13/04* (2013.01); *G01N 15/1436* (2013.01); *G06T 19/20* (2013.01); *G01N 2015/1445* (2013.01); *G06T 2219/2016* (2013.01)

(58) Field of Classification Search
None
See application file for complete search history.

(56) References Cited

U.S. PATENT DOCUMENTS

| | | | |
|---|---|---|---|
| 6,191,808 B1 | 2/2001 | Katayama et al. | |
| 6,195,205 B1 * | 2/2001 | Faris | ............................. 359/465 |
| 2006/0004541 A1 | 1/2006 | Miyamoto | |
| 2007/0035552 A1 | 2/2007 | Nozaki et al. | |

FOREIGN PATENT DOCUMENTS

| | | | | |
|---|---|---|---|---|
| JP | 03-251971 | | 11/1991 | |
| JP | 07-129792 | | 5/1995 | |
| JP | 2006-017497 | * | 6/2004 | ............. G01N 33/49 |
| JP | 2006-000127 | * | 1/2006 | ............... A61B 6/03 |
| JP | 2006-017497 | * | 1/2006 | ............. G01N 33/49 |
| JP | 2007-052508 | | 3/2007 | |

* cited by examiner

*Primary Examiner* — Amara Abdi
(74) *Attorney, Agent, or Firm* — Sony Corporation (57) ABSTRACT

The present invention provides a 3D data analysis apparatus and a 3D data analysis method.

A 3D data analysis apparatus including a data storage unit that stores measurement data of microparticles, an input unit that selects three kinds of variables independent of the measurement data, a data processing unit that calculates positions and graphics in a coordinate space with the three kinds of variables being coordinate axes and creates a 3D stereoscopic image that represents a characteristic distribution of the microparticles, and a display unit that displays the 3D stereoscopic image, and the 3D data analysis apparatus variably sets a separate area in the coordinate space on the basis of an input signal from the input unit and displays the area in the 3D stereoscopic image.

9 Claims, 11 Drawing Sheets

3D DATA ANALYSIS APPARATUS AND 3D DATA ANALYSIS METHOD

CROSS REFERENCES TO RELATED APPLICATIONS

The present application is a national stage of International Application No. PCT/JP2011/077196 filed on Nov. 25, 2011 and claims priority to Japanese Patent Application No. 2010-269945 filed on Dec. 3, 2010, the disclosure of which is incorporated herein by reference.

BACKGROUND

The present invention relates to a 3D data analysis apparatus and a 3D data analysis method. More specifically, the present invention relates to a 3D data analysis apparatus and the like capable of specifying microparticles to be analyzed in a 3D stereoscopic image.

To analyze microparticles including biologically relevant particles such as cells, microbes, and liposomes and synthetic particles such as latex particles, gel particles, and particles for industrial use, a microparticle measurement apparatus is used which introduces a dispersion liquid of microparticles in a flow channel and measures the microparticles optically, electrically, or magnetically.

As an example, there is a particle analyzer that distinguishes synthetic particles on the basis of sizes or shapes. Examples of a parameter (variable) which can be measured by the particle analyzer include an elemental composition and a particle diameter of a microparticle.

Further, to analyze biologically relevant particles, a flow cytometer (flow cytometry) is used. Examples of a parameter which can be measured by the flow cytometer include forward scattered light (FS), side scatter (SS), fluorescent light (FL), and impedance of microparticles. The forward scattered light (FS), the side scatter (SS), and the fluorescent light (FL) are used as parameters that indicate an optical characteristic of a cell or a microbe (hereinafter, simply referred to as "cell"), and the impedance is used as a parameter that indicates an electrical characteristic of a cell.

Specifically, first, the forward scattered light is light that is scattered at a small angle in a forward direction with respect to an axis of laser light and includes scattered light, diffracted light, and refracted light of laser light which is generated on a surface of a cell. The forward scattered light is mainly used as a parameter that indicates the size of a cell. Next, the side scatter is light that is scattered at approximately 90 degrees with respect to an axis of laser light and is scattered light of laser light that is generated in a granule or a core inside a cell. The side scatter is mainly used as a parameter that indicates an internal structure of a cell. Further, the fluorescent light is light that is generated from a fluorochrome labeled to a cell and is used as a parameter that indicates existence or nonexistence of a cell surface antigen recognized by a fluorochrome-labeled antibody, the amount of a nucleic acid to which a fluorochrome is combined, or the like. Furthermore, the impedance is measured by an electrical resistance method and used as a parameter that indicates a cell volume.

To analyze measurement data in a flow cytometer, a data analysis apparatus is used in which measurement values of cells are plotted with these measurement parameters being as axes, thereby creating a diagram that shows a characteristic distribution of the cells in a cell population. A one-dimensional distribution chart with the use of one measurement parameter is called as a histogram, which is created with an X axis indicating the measurement parameter, and a Y axis indicating the number of cells (count). Further, a two-dimensional distribution chart in which two measurement parameters are used is called as a cytogram, which is created by plotting cells on the basis of the measurement values in a coordinate plane with the X axis indicating one measurement parameter and the Y axis indicating the other measurement parameter.

The cell population as a sample includes unnecessary cells not to be analyzed, so the analysis of the measurement data is performed after a cell small population to be analyzed is selected from the cell population as the sample. The cell small population to be analyzed is selected by specifying an area in which the cell small population exists on the histogram or the cytogram. This operation is called as "gating" because cells as targets are enclosed in an area specified on the histogram or the cytogram.

On the histogram with one measurement parameter as an axis or on the cytogram with one combined measurement parameter as axes, the cell small population to be analyzed and unnecessary cells may exist in an overlapped area in some cases. For example, when a lymphocyte is analyzed with human peripheral blood as a sample, on a cytogram with a forward scattered light (FS) and a side scatter (SS) used for axes, a part of monocyte exists in the same area as the lymphocyte in some cases. Therefore, when performing gating, a user has to specify an area in which only lymphocyte exists so as not to enclose the monocyte.

In order to specify an area so that only a cell small population to be analyzed is enclosed without enclosing unnecessary cells, conventionally, a user has to perform gating while referring to a plurality of histograms or cytograms. Along with improvement of the performance of a flow cytometer, the number of parameters that can be measured is increased, so the user has to refer to more histograms or cytograms. Further, at this time, the user is requested to perform a gating operation while imaging a three-dimensional distribution chart (3D distribution chart) in which two cytograms are combined.

To assist the user in performing the gating operation, Patent Document 1 proposes "an analysis apparatus including a measurement data obtaining means for obtaining first, second, and third measurement data items from an analyte, a 3D distribution chart creating means for creating a 3D distribution chart that indicates a distribution of formed elements contained in the analyte with the first, second, and third measurement data items as axes, an area setting means for variably setting a separate area on the 3D distribution chart, and a reference distribution chart creating means for creating, with respect to formed elements that belongs to the separate area set by the area setting means, at least one of a 2D distribution chart with the first and second measurement data items used as the axes and a frequency distribution chart with the first measurement data item used as the axis" (see, claim 9 of Patent Document 1). By the analysis apparatus, it is possible to set the separate area on the 3D distribution chart while referring to the 2D distribution chart (cytogram) and the frequency distribution chart (histogram) displayed along with the 3D distribution chart. It should be noted that the 3D distribution chart of the analysis apparatus is not viewed stereoscopically but is displayed two-dimensionally on a display.

In relation to the present invention, twin-lens stereo image technology (3D stereoscopic image technology) will be described. In the twin-lens stereo image, first, two images when an object is viewed with a right eye and a left eye are prepared. Then, these images are displayed at the same time, and an image for the right eye is presented only to the right eye, and an image for the left eye is presented only to the left eye. As a result, an image that appears in the eyes at a time when the object is viewed in a 3D space is reproduced, and a user is caused to stereoscopically view the object.

For a 3D display which allows a stereoscopic view, a (a) glasses type, a (b) glasses-free type, and a (c) viewer type are mainly adopted. The (a) glasses type includes an anaglyph type, a polarization filter type, and a time-sharing type. Further, the (b) glasses-free type includes a parallax barrier type and a lenticular type, and the (c) viewer type includes a stereoscope type and a head mount type.

CITATION LIST

Patent Document

Patent Document 1: Japanese Patent Application Laid-open No. 2006-17497

SUMMARY

Problem to be Solved by the Invention

As described above, conventionally, in the data analysis apparatus used for the flow cytometer, to enclose only the cell small population to be analyzed without enclosing unnecessary cells at the time of gating, it is necessary for a user to perform an operation while referring to a large number of histograms or cytograms or imaging a three-dimensional distribution chart obtained by combining two cytograms (3D distribution chart). Therefore, in the conventional data analysis apparatus, it takes long time to perform the gating operation, and in the case where the user is not proficient in the operation, unnecessary cells are mixed in, causing a problem in analysis accuracy.

In view of the above, it is an object of the present invention to provide a data analysis apparatus capable of performing an easy and instinctive gating operation without referring to a large number of histograms or cytograms or imaging a 3D distribution chart, and capable of performing analysis with high accuracy.

Means for Solving the Problem

To solve the above-mentioned problem, the present invention provides a 3D data analysis apparatus including a data storage unit to store measurement data of microparticles, an input unit to select three kinds of variables independent of the measurement data, a data processing unit to calculate positions and graphics in a coordinate space with the three kinds of variables being coordinate axes and create a 3D stereoscopic image that represents a characteristic distribution of the microparticles, and a display unit to display the 3D stereoscopic image, the 3D data analysis apparatus variably setting a separate area in the coordinate space on the basis of an input signal from the input unit and displaying the area in the 3D stereoscopic image.

By the 3D data analysis apparatus, it is possible to perform the gating of the microparticles and the microparticle small population to be analyzed in the coordinate space while stereoscopically viewing the 3D distribution chart with the arbitrarily selected three kinds of parameters being the coordinate axes.

Further, the present invention also provides a 3D data analysis method including the steps of selecting three kinds of variables independent of measurement data of microparticles, calculating positions and graphics in a coordinate space with the three kinds of variables being coordinate axes and creating a 3D stereoscopic image that represents a characteristic distribution of the microparticles, displaying the 3D stereoscopic image, and setting a separate area in the coordinate space in the 3D stereoscopic image.

In the present invention, the "microparticles" widely include biologically relevant particles such as cells, microbes, and liposomes, synthetic particles such as latex particles, gel particles, and particles for industrial use, and the like.

The cells include animal cells (hematopoietic cells or the like) and plant cells. The microbes include bacteria such as coli bacilli, viruses such as tobacco mosaic viruses, and fungi such as yeast. The biologically relevant particles include chromosomes, liposomes, mitochondrion, organelle (cell organelle), and the like that form various cells. Further, the biologically relevant particles can include biologically relevant polymer such as nucleic acids, proteins, and complexes of these. The particles for industrial use may be organic or inorganic polymeric materials, metal, or the like. The organic polymeric materials include polystyrene, styrene-divinylbenzene, polymethyl methacrylate, and the like. The inorganic polymeric materials include glass, silica, magnetic materials, and the like. The metal include gold colloid, aluminum, and the like. These microparticles generally have spherical forms but may be non-spherical forms. Further, the sizes, masses, and the like of these microparticles are also not limited particularly.

Effect of the Invention

According to the present invention, the data analysis apparatus is provided which is capable of performing the easy and instinctive gating operation without referring to a large number of histograms or cytograms or imaging a 3D distribution chart, and capable of performing analysis with high accuracy.

Additional features and advantages are described herein, and will be apparent from the following Detailed Description and the figures.

DETAILED DESCRIPTION

Figure 1:
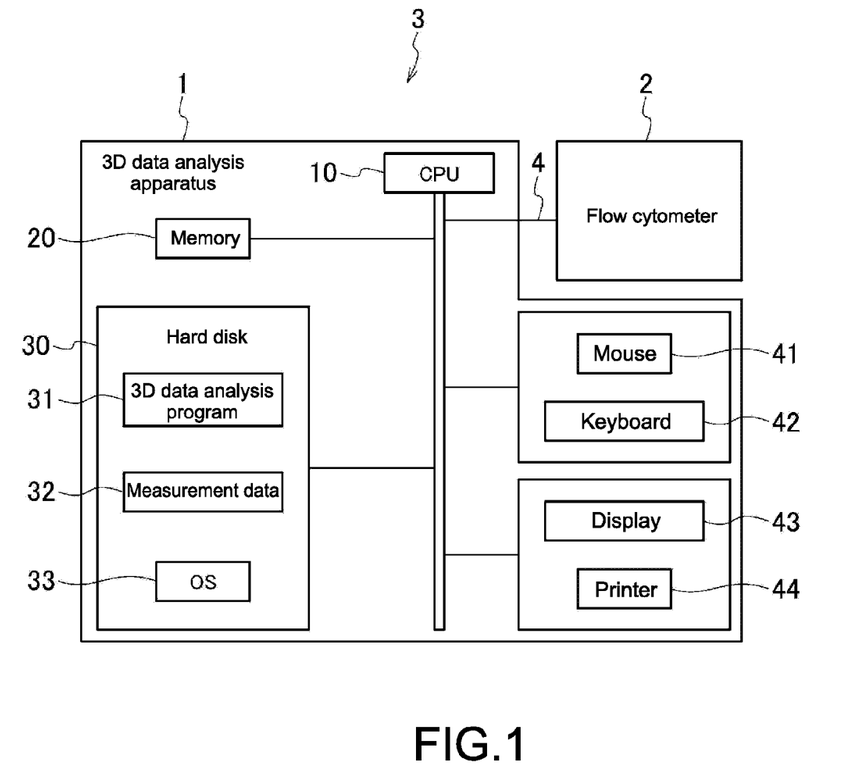
FIG. 1 is a block diagram for explaining the structure of a 3D analysis apparatus according to the present invention, which is provided so as to make a junction with a flow cytometer.
Figure 2:
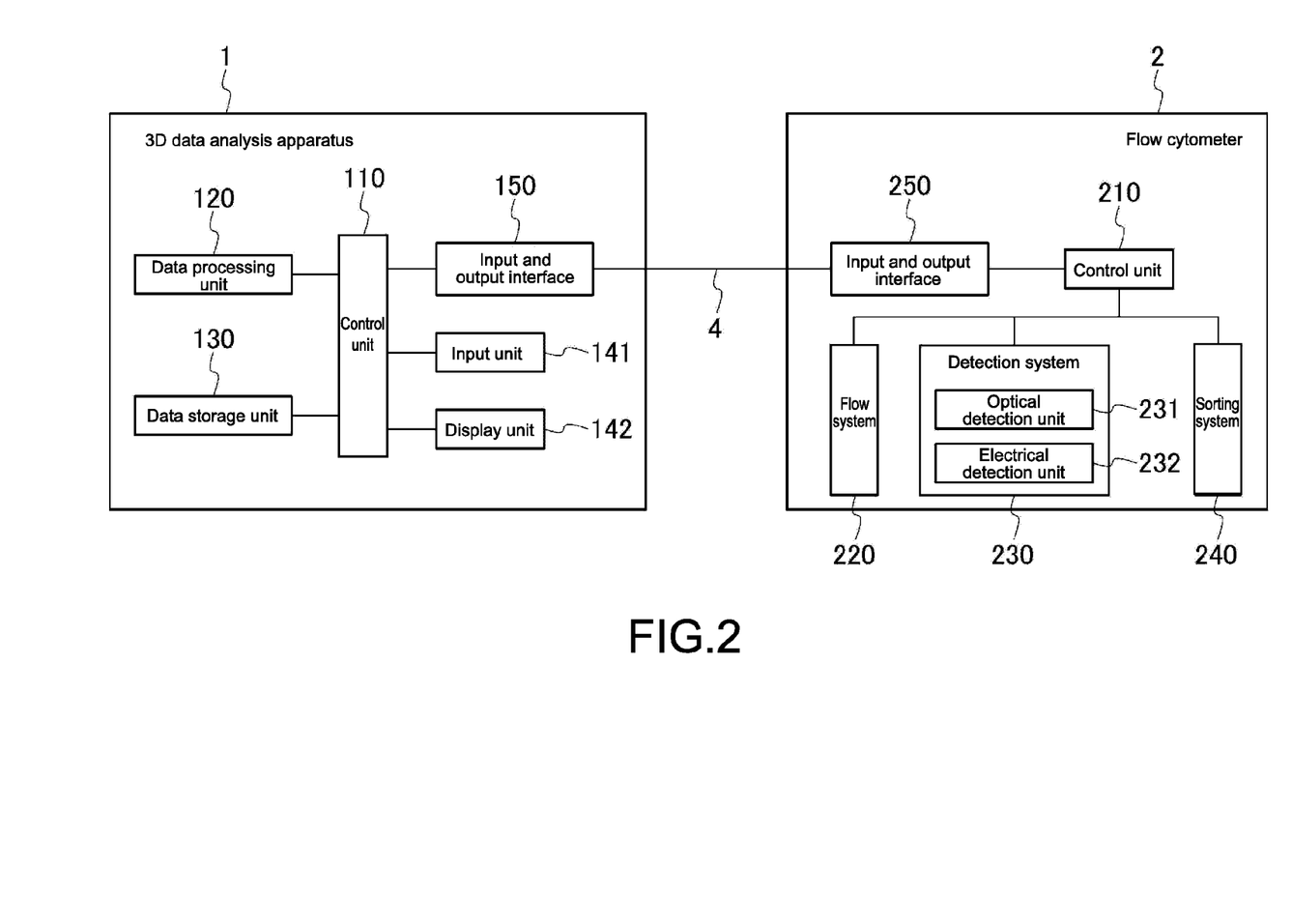
FIG. 2 is a block diagram for explaining the functional structure of the 3D analysis apparatus according to the present invention.

Hereinafter, preferred embodiments for carrying out the present invention will be described with reference to the drawings. It should be noted that the embodiments to be described below are an example of a representative embodiment of the present invention, so the scope of the present invention is not interpreted narrowly because of the embodiments. It should be noted that the description will be given in the following order.
1. Structure of 3D data analysis apparatus
2. Display of 3D stereoscopic image
3. Gating
4. Characteristics of 3D stereoscopic image
(4-1) shape of graphic
(4-2) shade process for graphic
(4-3) coordinate axis
(4-4) moving image
  1. Structure of 3D Data Analysis Apparatus FIG. 1 shows the structure of a 3D data analysis apparatus according to the present invention. Here, shown is an embodiment in which the 3D data analysis apparatus is provided contiguously with a microparticle measurement apparatus, thereby constituting a microparticle analysis system. Further, FIG. 2 shows the functional structure of the microparticle analysis system. Hereinafter, an example in which a flow cytometer is used as the microparticle measurement apparatus will be described.

The 3D data analysis apparatus denoted by reference numeral 1 in the figure constitutes a microparticle analysis system 3 by being connected to a flow cytometer 2 with a communication cable 4. The 3D data analysis apparatus 1 includes a central processing unit (CPU) 10, a memory 20, a hard disk 30, a user interface, and the like. In the hard disk 30, a 3D data analysis program 31, measurement data 32 of microparticles, an operating system (OS) 33, and the like are stored and held. The user interface includes an input device such as a mouse 41 and a keyboard 42 which receives an input of information from a user and an output device such as a display 43 and a printer 44 which outputs information to the user. It should be noted that an input device such as a stick controller and a pen tablet may be provided, instead of the mouse 41 and the keyboard 42 or along with these devices.

A data storage unit 130 (hard disk 30) stores the measurement data 32 of the microparticles (cells) which is output from the flow cytometer 2. The measurement data output from an input and output interface 250 of the flow cytometer 2 is input to an input and output interface 150 of the 3D data analysis apparatus 1 through the communication cable 4 and stored in a data storage unit 30 (hard disk 30).

The measurement data 32 is processed in a data processing unit 120. The data processing unit 120 starts the processing upon reception of an input from an input unit 141 (mouse 41, keyboard 42, or the like) by a user. That is, when the user selects and inputs three kinds of variables (parameters) independent of the measurement data 32, the data processing unit 120 creates a 3D distribution chart that represents a characteristic distribution of microparticles with the parameters selected being as the coordinate axes. The 3D distribution chart is created by plotting the microparticles in the coordinate space with the parameters selected being as the coordinate axes. The plotting of the microparticles are performed by calculating positions and a graphic in the coordinate space of the microparticles from measurement values of the parameters selected and drawing the graphic calculated on the position calculated.

Further, in the coordinate space of the 3D distribution chart created, the data processing unit 120 sets a separate area for performing gating for the microparticles on the basis of an input signal by the user from the input unit 141. The input by the user from the input unit 141 is performed by moving, deforming, or scaling up or down a pointer displayed in the 3D distribution chart with the use of the input device such as the mouse 41 and the keyboards 42.

Further, the data processing unit 120 performs processing (cluster analysis) of the measurement data of the microparticles that exist in the separate area set. Through the cluster analysis, for example, calculated is statistical data such as a rate of microparticles that exist in the separate area relative to all the microparticles, the number of microparticles that exist in the separate area, an average value, a standard deviation, a variation coefficient, and the like.

Here, the "parameters independent" refer to parameters which are selected from the forward scattered light (FS), the side scatter (SS), the fluorescent light (FL), the impedance, and the like of the microparticles and are different from each other. The fluorescent light (FL) can be dealt as a parameter different for each wavelength of fluorochrome labeled to the microparticles and represented by FL1, FL2 to FLn (n: 3 or more integer), or the like. As the three kinds of parameters independent, a combination of the forward scattered light (FS), the side scatter (SS), and the fluorescent light (FL1) or a combination of the forward scattered light (FS), the side scatter (SS), and the impedance are given as examples. In addition, the three kinds of parameters independent can be a combination arbitrarily selected from the measurement data.

The 3D distribution chart created by the data processing unit 120 and the separate area set in the coordinate space thereof are displayed as 3D stereoscopic images on an output unit 142 (display 43). The 3D stereoscopic image is a twin-lens stereo image to be described later in detail. The display of the 3D stereoscopic image on the output unit 142 may be performed in a rotated manner or a scaled-up or -down manner arbitrarily on the basis of an input signal of the user from the input unit 141 (mouse 41 or keyboard 42). Furthermore, a result of the cluster analysis by the data processing unit 120 is also output to the output unit 142 (display 43, printer 44, and the like). The statistical data may be displayed on the display unit 142 with numerical values or a graphic or may be printed, for example.

The flow cytometer 2 can have the same structure as the conventionally known apparatus or can be configured by appropriately modifying this, specifically, is constituted of a control unit 210, a flow system 220, a detection system 230, an input and output interface 250, and the like.

In a flow channel formed in a flow cell or micro chip, the flow system 200 causes a laminar flow of a sample liquid containing the microparticles to flow to the center of a laminar flow of a sheath liquid to arrange the microparticles in the laminar flow in a row. The detection system 230 obtains a parameter value that indicates the characteristic of the microparticles that are flown through the flow channel. Specifically, an optical detection unit 231 irradiates the microparticles flown with light, detects scattered light, fluorescent light, or the like generated from the microparticles, and obtains the intensity thereof. The optical detection unit 231 includes a laser light source, lens, a mirror, a filter, an area image pickup element such as a CCD and a CMOS element, a PMT (photo multiplier tube), or the like. Further, an electrical detection unit 232 includes an electrode provided so as to be opposed to the microparticles flown, and obtains an impedance, a capacitance value, an inductance, and the like of the microparticles. The flow cytometer 2 may be provided with a sorting system 240 for sorting the microparticles which are determined to have a desired characteristic as a result of the analysis. For the sorting system 240, for example, it is possible to adopt a system of ejecting a droplet containing the microparticles to a space outside the flow cell and controlling a moving direction of the droplet, thereby collecting only desired microparticles into a container.

The measurement values of the intensities of the scattered light, the fluorescent light, and the like detected in the detection system 230 or the measurement values of the impedance, the capacitance value, the inductance, and the like are converted into electrical signals and output from the input and output interface 250 as the measurement data.

2. Display of 3D Stereoscopic Image

Figure 3:
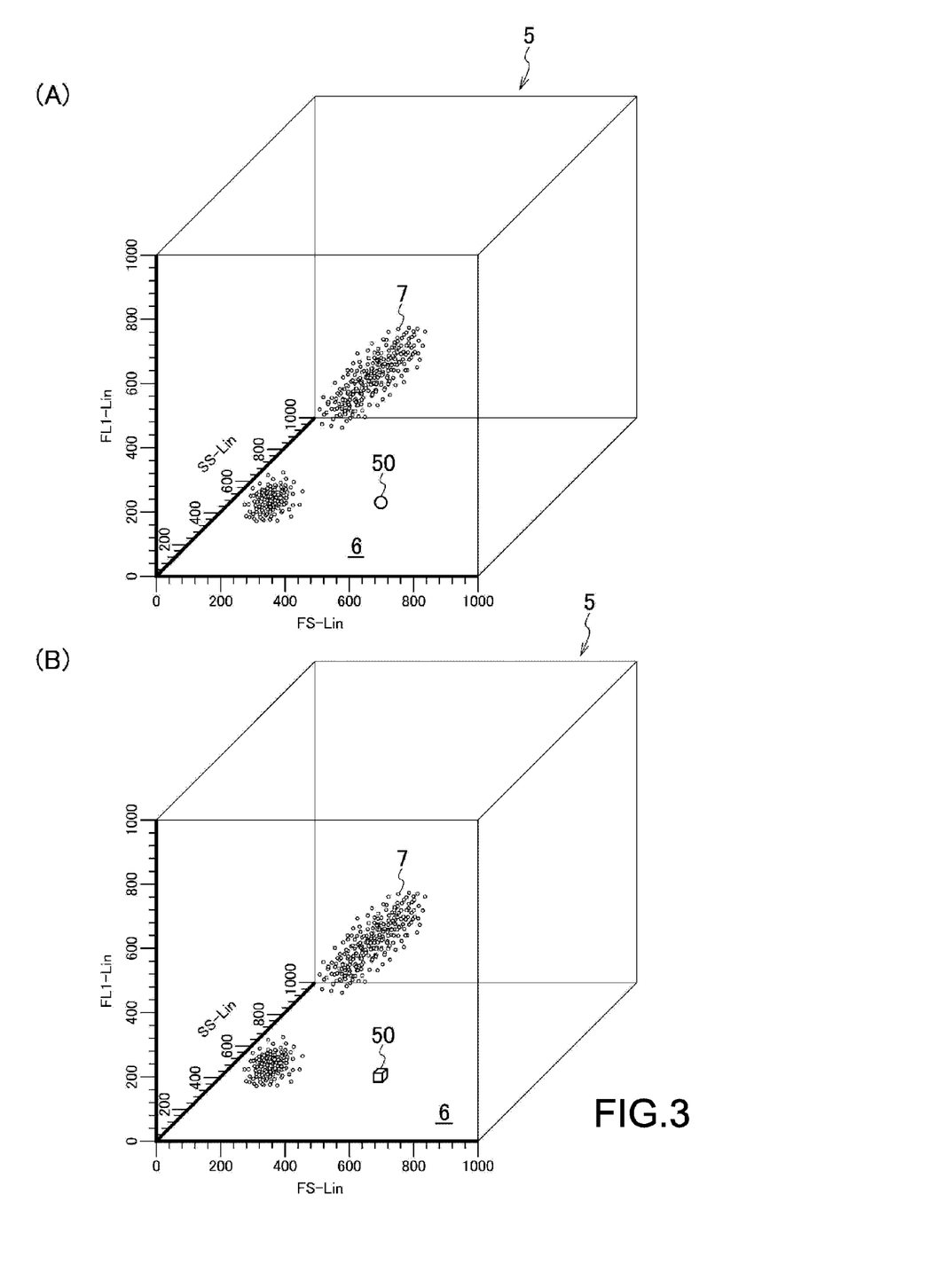
FIG. 3 is a schematic diagram for explaining 3D distribution charts displayed by the 3D data analysis apparatus according to the present invention.

FIG. 3 schematically shows 3D distribution charts displayed by the 3D data analysis apparatus according to the present invention. The 3D distribution charts are displayed as 3D stereoscopic images on the display unit 142 and can be stereoscopically visually confirmed by a user.

A 3D distribution chart 5 shows a characteristic distribution of the microparticles in a coordinate space 6 with the three kinds of parameters selected by a user being as the coordinate axes. In the 3D distribution chart 5, at positions calculated from the measurement values of the parameters selected, graphics 7 corresponding to the respective microparticles are drawn.

In the figure, the case where the three kinds of parameters are a combination of the forward scattered light (FS-Lin: X axis), the side scatter (SS-Lin: Y axis), and a first fluorescent light (FL1-Lin: Z axis) is given as an example. The parameters used for the respective coordinate axes can be a combination selected arbitrarily. For example, the first fluorescent light (FL1), a second fluorescent light (FL2), and an impedance can be used for the X axis, the Y axis, and the Z axis, respectively.

In the coordinate space 6 of the 3D distribution chart 5, a pointer 50 used for a setting of the separate area at the time when the gating for the microparticles is performed is displayed. The pointer 50 can also be stereoscopically visually confirmed by the user in the 3D stereoscopic image. The pointer 50 is arbitrarily moved, deformed, or scaled up or down in the coordinate space 6 by an input signal of a user from the input unit 141.

The shape of the pointer 50 is not particularly limited as long as the shape thereof is visually confirmed as a predetermined 3D shape at the time of a stereoscopic observation of the 3D stereoscopic image, and for example, a spherical shape as shown in (A) of FIG. 3 or a cubic shape as shown in (B) of FIG. 3 can be used.

Figure 4:
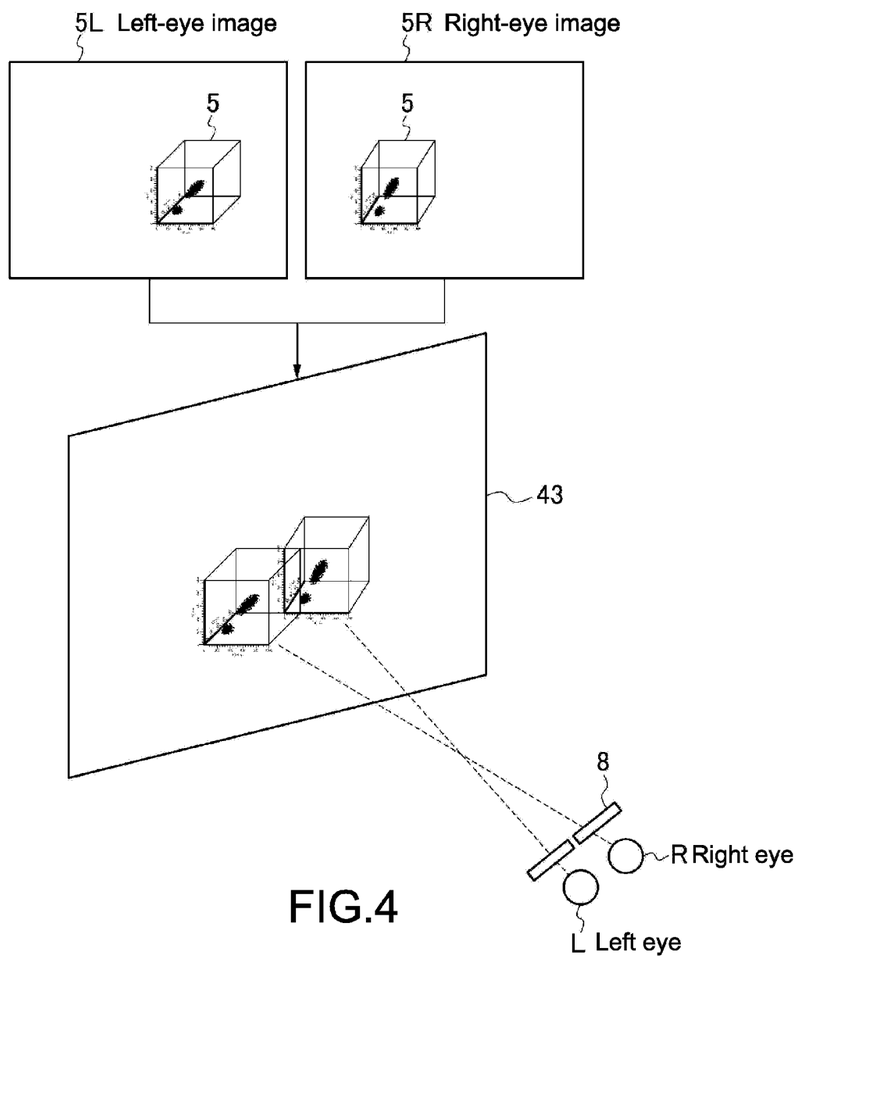
FIG. 4 is a schematic diagram for explaining a twin-lens stereo image (3D stereoscopic image) displayed by the 3D data analysis apparatus according to the present invention.

The 3D stereoscopic display of the 3D distribution chart is performed with a twin-lens stereo image. FIG. 4 schematically shows a twin-lens stereo image displayed by the 3D data analysis apparatus according to the present invention.

When a user selects the parameters, the data processing unit 120 creates the 3D distribution chart 5 and creates an image at a time when the distribution chart is viewed with the left eye (left-eye image 5L) and an image when viewed with the right eye (right-eye image 5R). The output unit 142 (display 43) displays the left-eye image 5L and the right-eye image 5R at the same time, and separate presentation is performed so that the left-eye image 5L is presented only to the left eye, and the right-eye image 5R presented only to the right eye.

For example, in a time-division system, which is one of the glasses type, the separation presentation can be performed by alternately displaying the left-eye image 5L and the right-eye image 5R with a minute time difference and causing shutter glasses 8 to be synthesized with this. In addition, for the separation distribution, another glasses type such as an anaglyph type and a polarization filter type, the glasses-free type such as a parallax barrier type and a lenticular type, and the viewer type such as a stereoscope type and a head mount type may be used.

By performing the separation presentation of the left-eye image 5L and the right-eye image 5R, the display 43 reproduces an image seen in the eyes at the time when the 3D distribution chart is viewed in the 3D space and causes a user to stereoscopically view the distribution chart.

3. Gating

Figure 5:
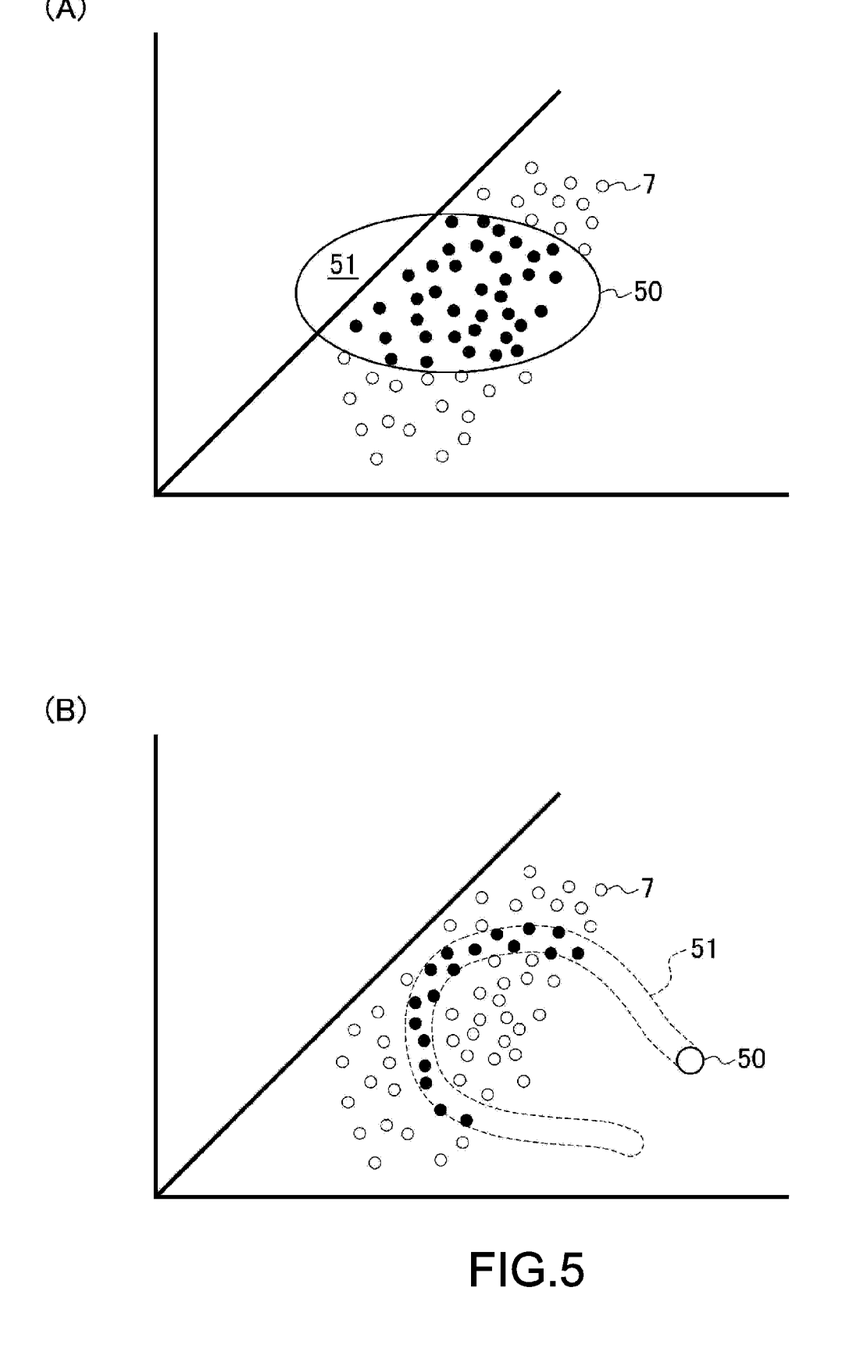
FIG. 5 is a schematic diagram for explaining specific examples of a separate area which can be set in the 3D data analysis apparatus according to the present invention.

The setting of the separate area for performing gating of the microparticles is performed by moving, deforming, or scaling up or down the pointer 50 displayed in the 3D distribution chart with the input device such as the mouse 41 and the keyboard 42. The separate area is set in an internal space of the pointer 50 that has been subjected to moving or the like. FIG. 5 shows specific examples of the separate areas which can be set.

(A) of FIG. 5 shows a separate area 51 set in the internal space of the pointer 50 which has an oval ball shape. The separate area 51 can be set by moving the pointer 50 shown in (A) of FIG. 3 to an area where the graphics 7 corresponding to the microparticles to be analyzed exist, deforming the pointer from a precise circle to an oval ball and enlarging the pointer, and entirely or partially matching the area with the internal space of the pointer 50. A plurality of separate areas 51 can be set, and two or more microparticle small populations to be analyzed can be enclosed in the separate areas.

Further, (B) of FIG. 5 shows the separate area 51 continuously set along a track of the internal space of the pointer 50 moved. The separate area 51 can be set by moving the pointer 50 shown in (A) of FIG. 3 so that the internal space thereof passes through the area where the graphics 7 corresponding to the microparticles to be analyzed exist and entirely or partially matching the area with the track of the internal space of the pointer. It is possible to set the plurality of separate areas 51 with discontinuous two or more tracks and to enclose two or more microparticle small populations to be analyzed in the respective separate areas.

The pointer 50 is deformed into any shape, scaled up or down into any size (volume), and moved in the 3D distribution chart, to enclose the graphics 7 corresponding to the microparticles to be analyzed in the separate area 51 set in the internal space of the pointer 50. At this time, the graphics 7 enclosed in the separate area may be displayed in the 3D stereoscopic image with a color (hue, chroma, brightness) different from the graphics 7 that exist outside the separate area 51. In FIG. 5, the graphics that have been subjected to the gating in the separate area 51 is indicated in black, and the graphics 7 outside the separate area is indicated in white.

Figure 6:
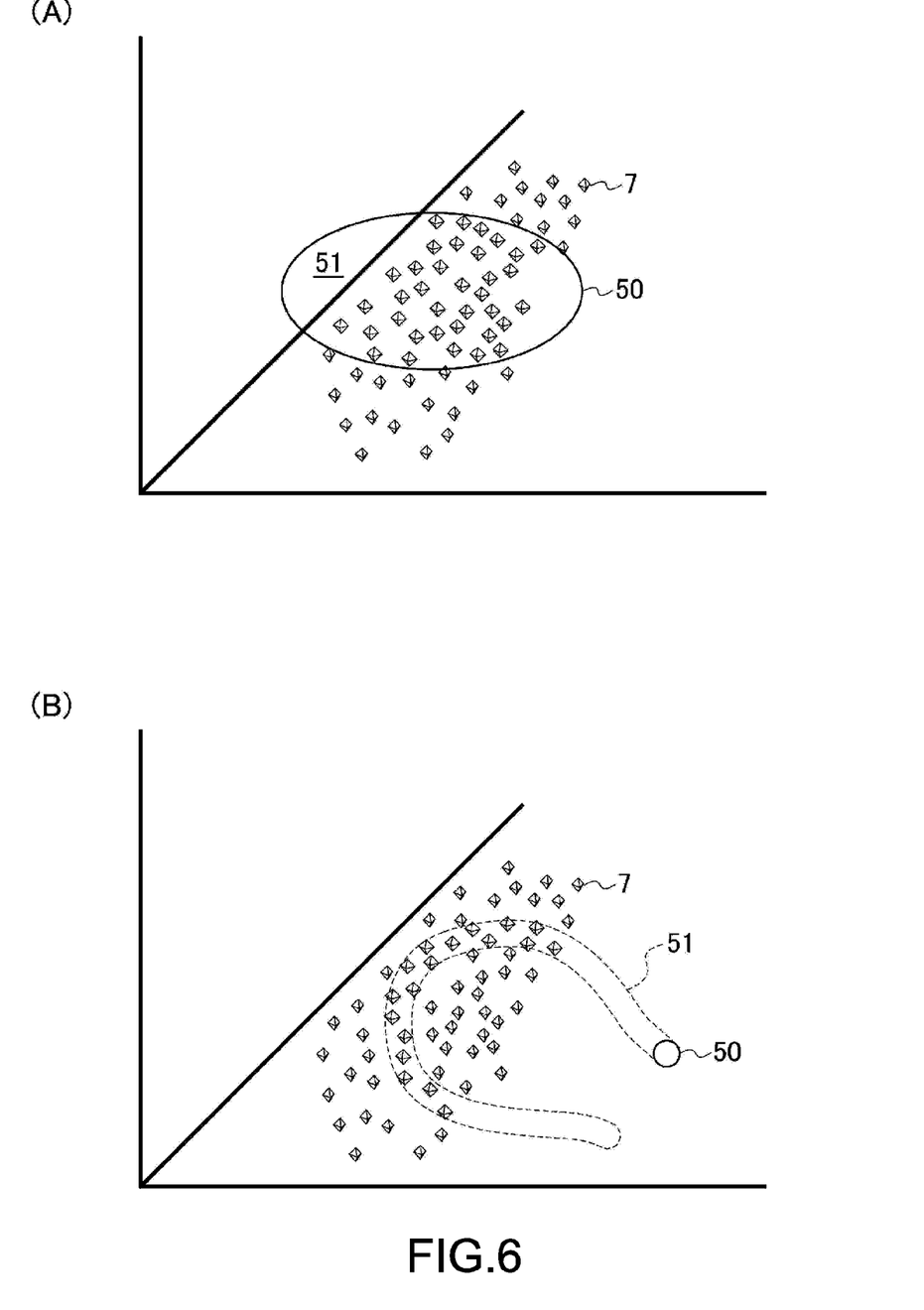
FIG. 6 is a schematic diagram for explaining specific examples of a separate area which can be set in the 3D data analysis apparatus according to the present invention.

The graphics 7 enclosed in the separate area and the graphics 7 that exist outside the separate area 51 may be displayed in the 3D stereoscopic image with different shapes as shown in FIG. 6. In FIG. 6, the graphics 7 that have been subjected to the gating in the separate area 51 are indicated in the forms of octahedrons (see, (B) of FIG. 7), and the graphics 7 outside the separate area are indicated in the forms of hexahedrons (see, (A) of FIG. 7).

The graphics 7 enclosed in the separate area and the graphics 7 that exist outside the separate area 51 may be displayed in different colors and different shapes. For example, in the case where the microparticles corresponding to the graphics 7 enclosed in the separate area are white blood cells, it is possible to indicate the graphics in color and shape similar to the white blood cells. In contrast, for example, in the case where the graphics 7 that exist outside the separate area 51 are red blood cells, it is possible to indicate the graphics in color and shape similar to the red blood cells.

Further, it is also possible to cause the graphics 7 (graphics 7 that exist outside the separate area 51) other than the graphics 7 that have been subjected to the gating not to be displayed in the 3D stereoscopic image. Alternatively, conversely, in the case where the graphics 7 corresponding to the microparticles not to be analyzed are subjected to the gating, it is possible to cause the graphics 7 (graphics 7 that exist in the separate area) that have been subjected to the gating not to be displayed in the 3D stereoscopic image.

As described above, in the 3D data analysis apparatus 1, it is possible for a user to perform the gating of the microparticles and microparticle small populations to be analyzed while stereoscopically viewing the 3D distribution chart with the arbitrarily selected three kinds of parameters being as the coordinate axes and viewing the pointer displayed in the coordinate space. Therefore, in the 3D data analysis apparatus 1, it is possible to easily and instinctively specify the microparticles and microparticle small populations to be analyzed on the distribution chart and perform the gating without referring to a lot of histograms or cytograms or imaging the 3D distribution chart as in the conventional way. In addition, the parameters used for the coordinate axes are arbitrarily combined to display the 3D distribution chart, with the result that it is possible to obtain information relating to the three characteristics of the microparticles with one graph. Thus, in the 3D data analysis apparatus 1, it is possible to perform the highly accurate gating for the microparticles and microparticle small populations to be analyzed and increase the efficiency of the gating operation by reducing the number of graphs to be referred to as compared to the conventional display with the histogram or cytogram.

4. Characteristics of 3D Stereoscopic Image

Hereinafter, the characteristics of the 3D stereoscopic image displayed by the 3D data analysis apparatus according to the present invention will be described in order.

(4-1) Shape of Graphic

The graphics corresponding to the microparticles, which are each denoted by the reference numeral 7 in FIG. 3, are calculated as polyhedrons constituted of polygons each having a predetermined shape and displayed in the 3D stereoscopic image. As described above, on the basis of the measurement values of the parameters selected by a user, the data processing unit 120 calculates the positions and the graphics 7 of the microparticles in the coordinate space and creates the 3D distribution chart. At this time, by calculating the graphic 7 as the polyhedron constituted of the polygons having the predetermined shape, it is possible to reduce a calculation load in the data processing unit 120. Further, by displaying, in the 3D stereoscopic image, the graphic 7 as the polyhedron constituted of the polygons having the predetermined shape, it is possible to increase the stereoscopic effect of an image when the image is stereoscopically viewed.

Figure 7:
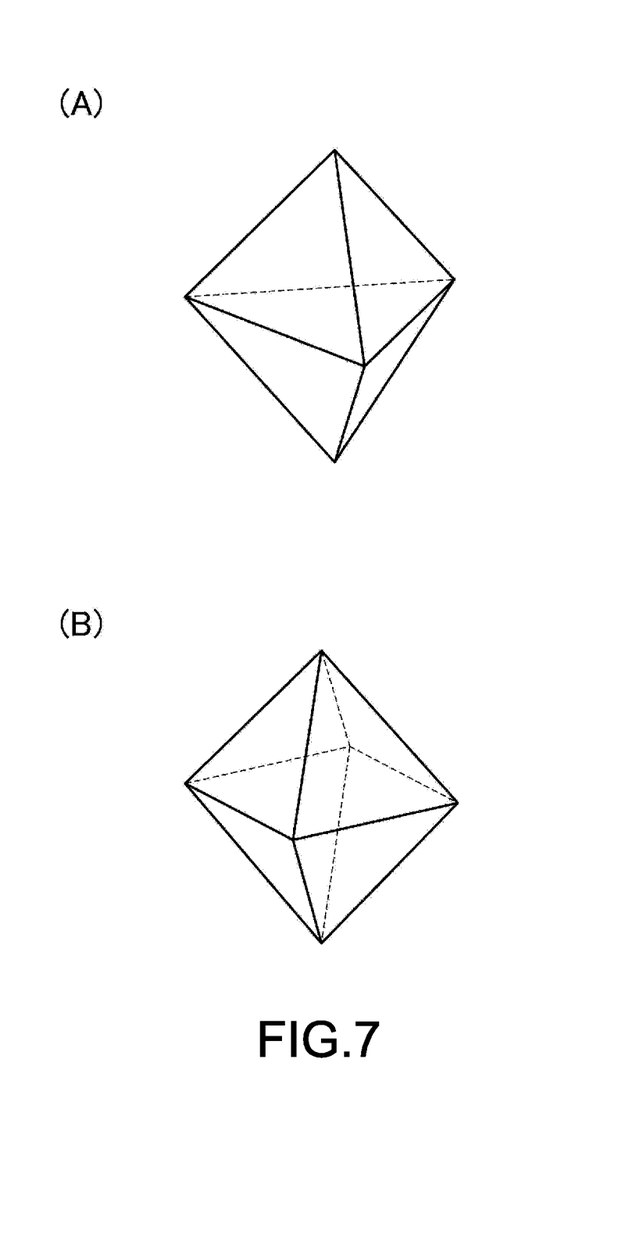
FIG. 7 is a schematic diagram for explaining shapes of graphics corresponding microparticles in the 3D stereoscopic image.

As the polyhedron constituted of the polygons having the predetermined shape, for example, a hexahedron constituted of six triangular polygons as shown in (A) of FIG. 7 or an octahedron constituted of eight polygons as shown in (B) of FIG. 7 can be employed. The shapes of the graphics 7 can be set as shapes different inside and outside the separate area, and are not particularly limited as long as a polyhedron constituted of polygons each having a predetermined shape is provided. In a viewpoint of the stereoscopic effect and the reduction of the calculation load, the hexahedron or the octahedron is preferable.

(4-2) Shade Process for Graphic

In the 3D stereoscopic image, the graphics 7 observed forward when stereoscopically viewed are indicated with increased shading, and the graphics 7 observed backward are indicated with decreased shading. In this way, a process of changing the shading of the graphics 7 is referred to as a "shade process" hereinafter.

Figure 8:
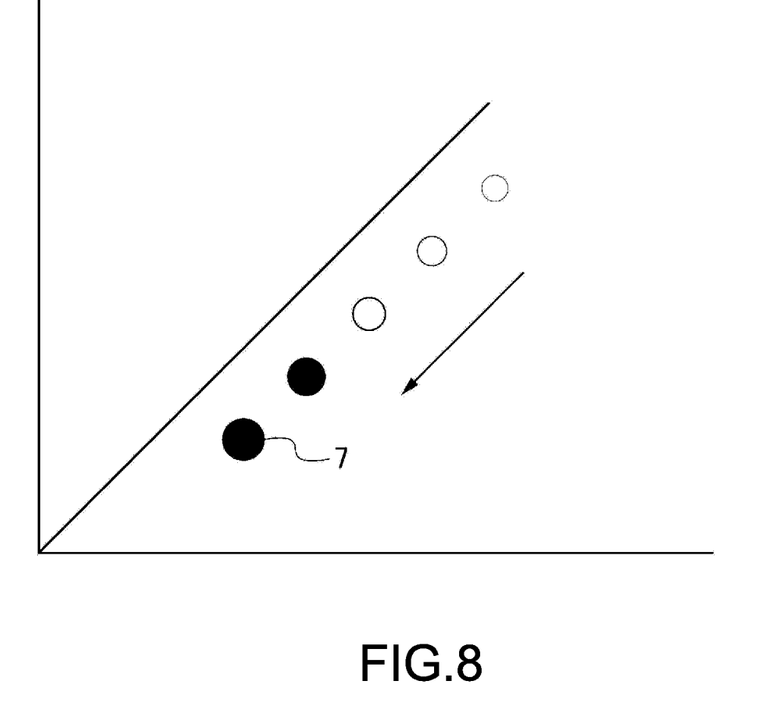
FIG. 8 is a schematic diagram for explaining a stereoscopic observation image of a graphic which is subjected to a shade process.

A conceptual diagram of a stereoscopic observation image (hereinafter, simply referred to as "stereoscopic image") of the graphic 7 which has been subjected to the shade process is shown in FIG. 8. Toward a direction of the arrow in the figure, the graphics 7 observed forward are darker, and the graphics 7 observed backward are paler. In this way, by performing the shade process for the graphics 7, a depth is given to the stereoscopic image of the 3D stereoscopic image, and the stereoscopic effect can be increased.

Figure 9:
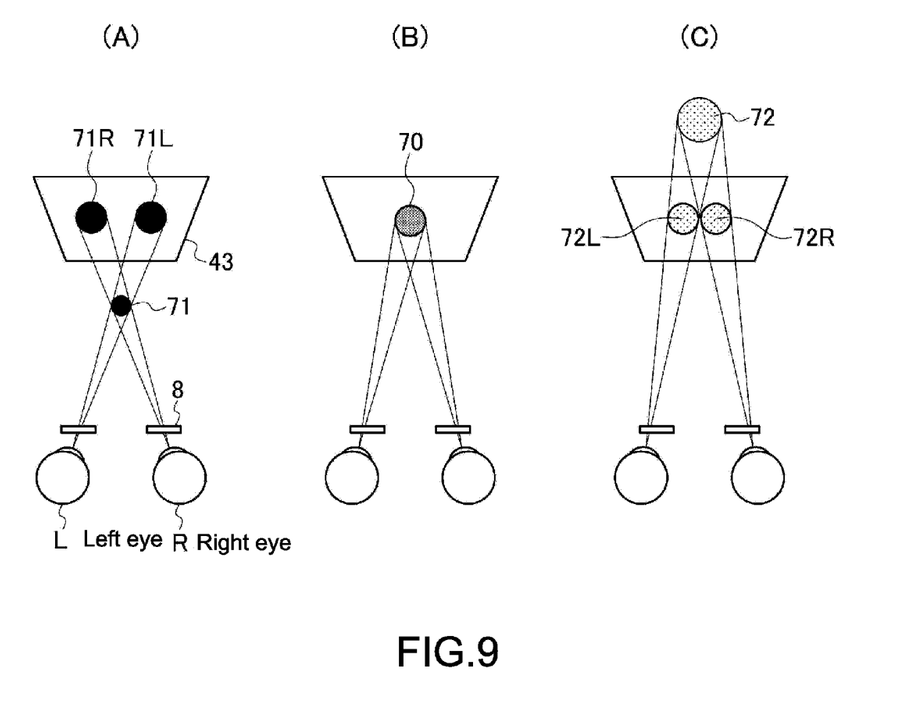
FIG. 9 is a schematic diagram for explaining a method of processing the shade process.

With reference to FIG. 9, the method of shade process will be described. On the display 43, a left-eye image and a right-eye image are displayed at the same time, and the left-eye image and the right-eye image of a graphic 70 observed at a position on a screen of the display 43 when stereoscopically viewed are displayed in a superimposed manner (see, (B) of FIG. 9).

In the case where the left-eye image displayed on the display 43 is positioned rightward as compared to the right-eye image (see, (A) of FIG. 9), the graphic is stereoscopically viewed forward as compared to the position on the screen of the display 43. The stereoscopic image of the graphic observed in a pop-up manner from the screen position is denoted by the reference numeral 71 in the figure, and the left-eye image and the right-eye image of the graphic 71 displayed on the display 43 are denoted by the symbols 71L and 71R, respectively. On the other hand, in the case where the left-eye image displayed on the display 43 is positioned leftward as compared to the right-eye image (see, (C) of FIG. 9), the graphic is stereoscopically viewed backward from the position on the screen of the display 43. The stereoscopic image of the graphic observed in a pop-up manner from the screen position is denoted by the reference numeral 72, and the left-eye image and the right-eye image of the graphic 71 displayed on the display 43 are denoted by the symbols 72L and 72R, respectively.

In the shade process, the left-eye image 71L and the right-eye image 71R of the graphic 71 observed forward are displayed to be darker, and the left-eye image 72L and the right-eye image 72R of the graphic 72 observed backward are displayed to be paler.

(4-3) Coordinate Axes

Figure 10:
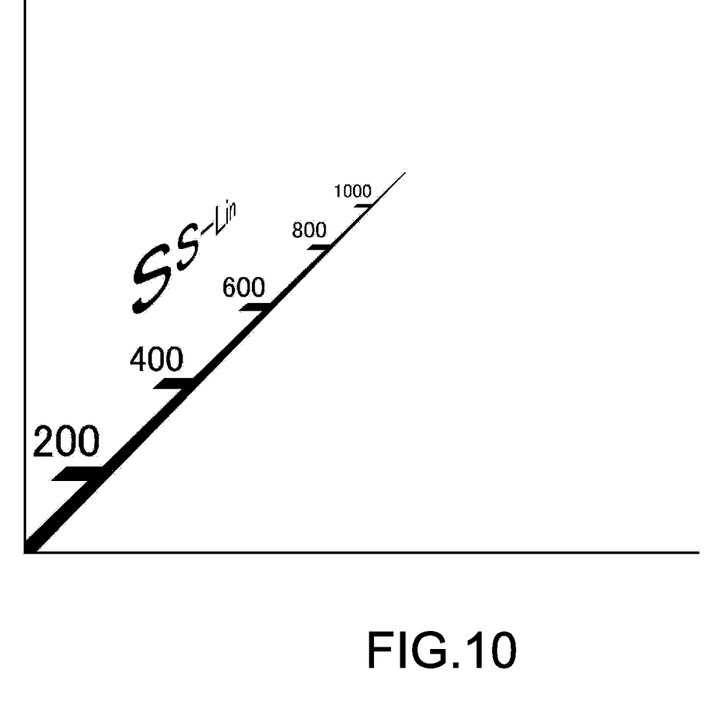
FIG. 10 is a conceptual diagram for explaining a stereoscopic observation image of coordinate axes.
Figure 11:
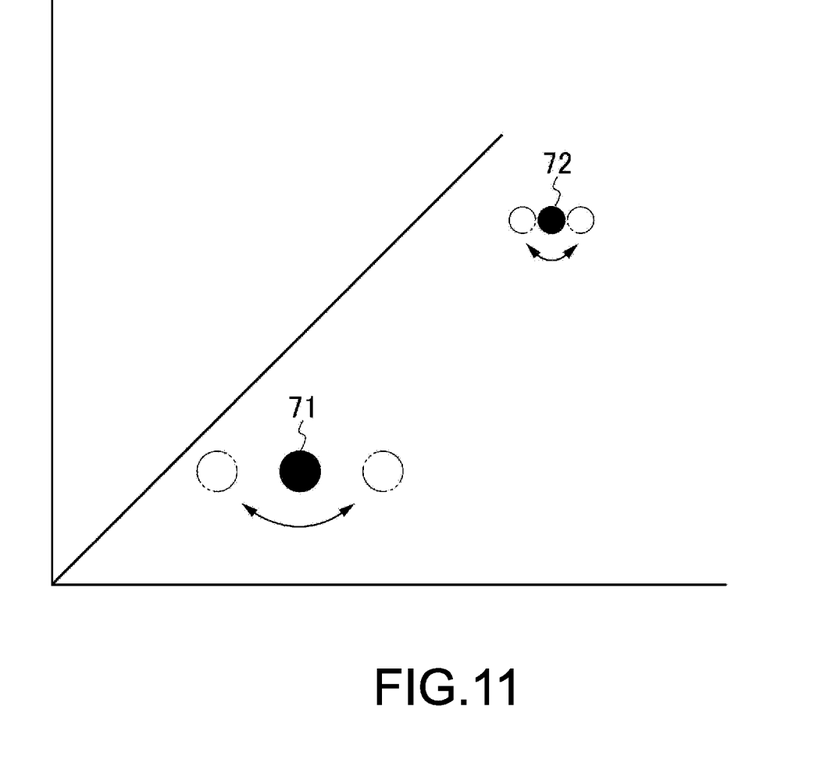
FIG. 11 is a conceptual diagram for explaining a stereoscopic observation image of a moving image obtained by swinging a graphic corresponding to the microparticle.

In the 3D stereoscopic image, the coordinate axis is displayed to be thicker as a part observed forward when the stereoscopic viewing is performed, and the coordinate axis is displayed to be thinner as a part observed backward. A conceptual diagram of a stereoscopic image of the coordinate axis having a varied thickness is shown in FIG. 10. In this way, by changing the thickness of the coordinate axis, it is possible to increase the stereoscopic effect by giving a depth to the stereoscopic image of the 3D stereoscopic image.

Further, as shown in FIG. 10, scale intervals of the coordinate axis are set to be wider as a part observed forward when the stereoscopic viewing is performed, and the scale intervals thereof are set to be narrower as a part observed backward, with the result that a further depth can be given to the stereoscopic image. Furthermore, the name of the coordinate axis (SS-Lin in the figure) and the characters of the scale values (200, 400, 600, 800, 1000, in the figure) are displayed to be larger toward the front and displayed to be smaller toward the back, with the result that the same effect is obtained. It should be noted that the process of changing the thickness of the coordinate axis, the size of the scale intervals, and the size of the characters can also be performed through an application of the shade process described above.

(4-4) Moving Image

As described above, the display of the 3D stereoscopic image to the output unit 142 (display 43) may be performed by arbitrarily rotating or scaling up or down on the basis of an input signal of the user from the input unit 141 (mouse 41, keyboard 42, or the like). When the 3D stereoscopic image is rotated, as shown in FIG. 3, it is preferable that the coordinate axes are displayed on each side of the 3D configuration (cube in the figure) that forms the coordinate space 6. The 3D configuration of the coordinate space 6 becomes clear because of these coordinate axes, so a change of the direction of the 3D distribution chart at the time when the 3D stereoscopic image is rotated is easily recognized.

The 3D stereoscopic image displayed on the display 43 may be rotated optionally by an input from a user or may be always rotated slowly in a certain direction. By displaying the 3D stereoscopic image as a moving image that is always rotated, the stereoscopic effect can be increased as compared to the display with a still image.

Further, the 3D stereoscopic image displayed on the display 43 may be displayed with such a moving image that the graphics corresponding to the microparticles are swung. At this time, as compared to graphics observed backward when the stereoscopic viewing is performed, graphics observed forward are swung more intensely. A conceptual diagram of the stereoscopic images of the graphics to which the swinging operation is given is shown in FIG. 10. The graphics 71 and 72 are swung rightward and leftward as indicated by the arrows in the figure, and a rightward and leftward swinging range is larger for the graphic 71 observed forward and smaller for the graphic 72 observed backward. In this way, as compared to the graphic observed backward when the stereoscopic viewing is performed, the graphic observed forward is displayed in the more intensely swinging manner, with the result that the depth is given to the stereoscopic image of the 3D stereoscopic image, and the stereoscopic effect can be increased.

As described above, the 3D data analysis apparatus according to the present invention is devised to increase the stereoscopic effect of the 3D stereoscopic image displayed. Therefore, even in the case of the 3D distribution chart constituted of only points (graphics corresponding to the microparticles) and lines (coordinate axes), it is possible for a user to analyze the measurement data while preferably visually confirming the stereoscopic image and easily and instinctively specify the microparticles and the microparticle small population to be analyzed on the distribution chart.

INDUSTRIAL APPLICABILITY

By the 3D data analysis apparatus according to the present invention, it is possible to perform the easy, instinctive gating operation without referring to a lot of histograms or cytograms or imaging the 3D distribution chart and perform the analysis with high accuracy. Therefore, the 3D data analysis apparatus according to the present invention is used along with a flow cytometer, for example, and is usable to easily analyze characteristics of cells or microbes with high accuracy in the fields of medicine, public health, drug discovery, and the like.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF REFERENCE NUMERALS

1: 3D data analysis apparatus
10: central processing unit
110: control unit
120: data processing unit
130: data storage unit
141: input unit
142: display unit
150: input and output interface
2: flow cytometer
210: control unit
220: flow system
230: detection system
231: optical detection unit
232: electrical detection unit
240: sorting system
250: input and output interface
3: microparticle analysis system
30: hard disk
31: 3D data analysis program
32: measurement data
33: operating system
4: communication cable
41: mouse
42: keyboard
43: display
44: printer
5: 3D distribution chart
50: pointer
51: separate area
6: coordinate space
7: graphic
8: shutter glasses

The invention claimed is:

1. A 3D data analysis apparatus, comprising:
a data storage unit to store measurement data of microparticles;
an input unit to select three kinds of variables independent of the measurement data;
a data processing unit to calculate positions and graphics in a coordinate space with the three kinds of variables being coordinate axes and create a 3D stereoscopic image that represents a characteristic distribution of the microparticles; and
a display unit to display the 3D stereoscopic image, the 3D data analysis apparatus variably setting a separate area in the coordinate space on the basis of an input signal from the input unit and displaying the separate area in the 3D stereoscopic image,
wherein the separate area is set along a track of an internal space of a pointer moved in the coordinate space, so that the internal space thereof passes through the area where the graphics corresponding to the microparticles to be analyzed exist and entirely or partially matching the area with the track of the internal space of the pointer.

2. The 3D data analysis apparatus according to claim 1, wherein the pointer is visually confirmed as a predetermined 3D shape at a time of an observation of a stereoscopic image of the 3D stereoscopic image, and the input unit includes an input device that moves, deforms, or scales up or down the pointer in the coordinate space.

3. The 3D data analysis apparatus according to claim 2, wherein in the 3D stereoscopic image, the graphics that exist in the separate area are each displayed in a different color from the graphics that exist outside the separate area.

4. The 3D data analysis apparatus according to claim 2, wherein in the 3D stereoscopic image, the graphics that exist in the separate area are each displayed in a different shape from the graphics that exist outside the separate area.

5. The 3D data analysis apparatus according to claim 2, wherein in the 3D stereoscopic image, the graphics that exist in the separate area are set to be a non-display state.

6. The 3D data analysis apparatus according to claim 1, wherein the display means is a display, and the 3D data analysis apparatus comprise glasses for stereoscopically viewing the 3D stereoscopic image displayed on the display.

7. A microparticle analysis system being configured by contiguously providing the 3D data analysis apparatus according to claim 1 and a microparticle measurement apparatus.

8. A 3D data analysis method, comprising the steps of:
selecting three kinds of variables independent of measurement data of microparticles;
calculating positions and graphics in a coordinate space with the three kinds of variables being coordinate axes and creating a 3D stereoscopic image that represents a characteristic distribution of the microparticles;
displaying the 3D stereoscopic image; and
setting a separate area in the coordinate space in the 3D stereoscopic image,
wherein the separate area is set along a track of an internal space of a pointer moved in the coordinate space, so that the internal space thereof passes through the area where the graphics corresponding to the microparticles to be analyzed exist and entirely or partially matching the area with the track of the internal space of the pointer.

9. The 3D data analysis method according to claim 8, wherein the pointer is visually confirmed as a predetermined 3D shape at a time of an observation of a stereoscopic image of the 3D stereoscopic image, and the pointer is moved, deformed, or scaled up or down in the coordinate space.

* * * * *